United States Patent [19]

Wheaton

[11] Patent Number: 4,910,335
[45] Date of Patent: Mar. 20, 1990

[54] DECOLORIZATION OF ALKANESULFONIC AND ARENESULFONIC ACIDS

[75] Inventor: Gregory A. Wheaton, Logan Township, Gloucester County, N.J.

[73] Assignee: Pennwalt Corporation, Philadelphia, Pa.

[21] Appl. No.: 388,212

[22] Filed: Aug. 1, 1989

[51] Int. Cl.$^4$ ............... C07C 139/00; C07C 143/24
[52] U.S. Cl. .................................. 562/124; 562/45; 562/89; 562/92; 562/96
[58] Field of Search ................. 562/124, 96, 92, 89, 562/45

[56] References Cited

U.S. PATENT DOCUMENTS

| | | | |
|---|---|---|---|
| 2,502,619 | 4/1950 | Proell et al. | 260/429 |
| 3,232,975 | 2/1966 | Merkel | 562/45 |
| 3,269,927 | 8/1966 | Bost | 264/131 |
| 3,413,337 | 11/1968 | Bost | 260/513 |
| 3,479,398 | 11/1969 | Bost et al. | 260/513 |
| 3,666,797 | 5/1972 | Nagayama et al. | 260/513 |
| 3,997,575 | 12/1976 | Ogoshi et al. | 562/124 |
| 4,197,255 | 4/1980 | Baumann et al. | 260/513 |

OTHER PUBLICATIONS

*Chemical Abstracts*, 79:18083, (1973)—Japanese Kokai 73 22423.

*Primary Examiner*—Alan Siegel
*Attorney, Agent, or Firm*—Panitch Schwarze Jacobs & Nadel

[57] ABSTRACT

A method for decolorizing color contaminated alkanesulfonic or arenesulfonic acids represented by Formula I:

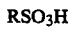

$$RSO_3H \qquad\qquad I$$

comprises mixing the color contaminated acid with an effective amount of a dialkanesulfonyl or diarenesulfonyl peroxide represented by Formula II:

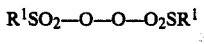

$$R^1SO_2-O-O-O_2SR^1 \qquad\qquad II$$

and allowing the mixture to stand at a temperature and for a period of time sufficient to allow the color of the acid to decrease to the desired level, wherein R in Formula I and R$^1$ in Formula II may each represent an alkyl radical or an aryl radical, with the proviso that R in Formula I may be the same as or different from R$^1$ in Formula II.

21 Claims, No Drawings

DECOLORIZATION OF ALKANESULFONIC AND ARENESULFONIC ACIDS

FIELD OF THE INVENTION

The present invention relates to a method for the preparation of alkanesulfonic or arenesulfonic acids with very light color. More specifically, this invention relates to the decolorization of color-contaminated alkanesulfonic or arenesulfonic acids.

BACKGROUND OF THE INVENTION

During the production of alkanesulfonic or arenesulfonic acids by methods known to those skilled in the art, the product acids are generally colored, ranging from light yellow to essentially black. Heretofore, various method have been employed to either prevent the formation of this color during the manufacture of the sulfonic acids or to remove the color from the product acids once they have been formed.

For example, U.S. Pat. No. 2,502,619 describes the purification of salts of alkanesulfonic acids to remove colloidal materials and coloring matter by heating the solid alkanesulfonic acid salts at temperatures between about 100° and 250° C., dissolving the thermally treated salt in water, and treating the resulting aqueous solution of the alkanesulfonic acid salt with a granular adsorbent, such as activated carbon. The present inventor has found that the coloring matter in anhydrous alkanesulfonic acid is not substantially removed by treatment with adsorbants, such as activated carbon, and that the dilution of the anhydrous sulfonic acid with water, in order to effect removal of the coloring matter by this method, is not desirable.

U.S. Pat. No. 3,269,927, discloses that color bodies and color-forming materials can be effectively removed from alkanesulfonic acids by subjecting the color-contaminated sulfonic acid to a direct current electrical field. However, this method employs undesirably high current densities (e.g., 10–120 amps). The present inventors have found that using this method results in the formation of sulfuric acid, which is an undesirable impurity in the resultant anhydrous alkanesulfonic acids.

According to U.S. Pat. Nos. 3,413,337 and 3,479,398, alkanesulfonic acids of improved color can be produced by the reaction of saturated hydrocarbons with sulfur dioxide and a catalyst, either by using ozone as the reaction initiator, or by further treating the product alkanesulfonic acids from the sulfoxidation reaction with ozone after removal of the acids from the sulfoxidation reactor. However, the use of ozone for the decolorization of the sulfonic acids requires the use of very high voltages and specialized equipment for the generation of the ozone. This may result in the formation of undesirable impurities, such as sulfuric acid, in the decolorized sulfonic acids.

U.S. Pat. No. 3,666,797, describes a method for the production of light-colored paraffin sulfonic acids through the sulfoxidation of paraffinic hydrocarbons. In this method, the product sulfonic acids are separated from by-product sulfuric acid and concentrated by evaporation of water in the presence of hydrogen peroxide, in order to prevent the formation of extraneous color bodies. However, the use of hydrogen peroxide to decolorize the anhydrous sulfonic acids is undesirable, as this method introduces water into the anhydrous acids and can result in the formation of sulfuric acid.

U.S. Pat. No. 4,197,255 describes the bleaching of $C_{8-22}$ olefinic sulfonic acids in an alkaline solution at a pH of approximately 10–14 and a temperature of 30°–80° C., using hydrogen peroxide, chlorine, alkaline metal chlorites, or alkaline metal hypochlorites as bleaching agents. However, this method employs an alkaline medium which is not applicable to the decolorization of anhydrous sulfonic acids. Also, the use of chlorine oxides would introduce undesirable impurities into the anhydrous sulfonic acids.

In Japanese Patent Application (OPI) No. 73/22423 (Chemical Abstracts, 79, 18083 (1973)) it is reported that substantially anhydrous methanesulfonic acid can be decolorized by the passage of chlorine through the acid for two (2) hours at a 135° C. However, this method also introduces undesirable impurities into the sulfonic acid, such as chlorine and/or chloride ions. Also, other impurities, such as sulfuric acid and chlorinated methane sulfonic acid, may be formed during the decolorization treatment.

Therefore, in view of the deficiencies of the known methods as described above, it would be desirable to have a method for decolorizing alkanesulfonic or arenesulfonic acids which does not involve the addition of water or other undesirable impurities to the purified anhydrous sulfonic acid, and which does not result in the formation of undesirable impurities during the decolorization of the sulfonic acid.

SUMMARY OF THE INVENTION

According to the present invention, there is provided a method for decolorizing a color contaminated alkanesulfonic or arenesulfonic acid represented by Formula I:

$$RSO_3H \qquad \qquad I$$

which comprises mixing the color contaminated alkanesulfonic or arenesulfonic acid with an effective amount of a dialkanesulfnnyl or diarenesulfonyl peroxide represented by Formula II:

$$R^1SO_2-O-O-O_2SR^1 \qquad \qquad II$$

and allowing the mixture to stand at a temperature and for a period of time sufficient to allow the color of the alkanesulfonic or arenesulfonic acid to decrease to the desired level, wherein R in Formula I and $R^1$ in Formula II each represent an alkyl radical or an aryl radical, with the provision that R in Formula I may be the same as or different from $R^1$ in Formula II.

DETAILED DESCRIPTION OF THE INVENTION

The sulfonic acids which may be treated according to the process of this invention are those represented by Formula I:

$$RSO_3H \qquad \qquad I$$

wherein R may represent an alkyl radical containing from 1 to about 12 carbon atoms, such as, for example, methyl, ethyl, 1-propyl, 2-propyl, 1-butyl, 2-butyl, tertiary-butyl, iso-butyl, cyclohexyl, 1-octyl, dodecyl, trifluoromethyl and other polyhalogenated alkyl radicals, etc. R may also represent an aryl radical containing from 6 to about 18 carbon atoms, such as, for example, phenyl, tolyl, butylphenyl, dodecylphenyl, naphthyl, etc.

The dialkanesulfonyl or diarenesulfonyl peroxides which may be used in the process of the present invention, are those represented by Formula II:

$$R^1SO_2-O-O-O_2SR^1 \qquad \text{II}$$

wherein $R^1$ is an alkyl or aryl radical such as defined above for the alkanesulfonic or arenesulfonic acid of Formula I.

Among these, the preferred sulfonic acid and dialkanesulfonic peroxides are mehanesulfonic acid and dimethanesulfonyl peroxide, respectively.

The alkyl or aryl radical $R^1$ in the dialkanesulfonyl or diarenesulfonyl peroxide represented by Formula II may be the same as or different from the alkyl or aryl radical R in the alkanesulfonic or arenesulfonic acid being treated and represented by Formula I. However, it is preferred that the alkyl or aryl radical $R^1$ in Formula II be the same as the alkyl or aryl radical represented by R in Formula I (i.e., the alkanesulfonic or arenesulfonic acid being decolorized).

Generally, the sulfonic acids which may be effectively decolorized by the present method are not limited. The present method may be used to decolorize both aqueous solutions of sulfonic acid (e.g., 70 wt. % alkanesulfonic acid), as well as substantially anhydrous sulfonic acids. "Substantially anhydrous" as used in the present application represents sulfonic acids containing less than about 1 weight percent and preferably less than about 0.5 weight percent water. The time required for effective decolorization of aqueous sulfonic acid solutions is longer than that required for substantially anhydrous sulfonic acids, due to the decreased solubility of the peroxide in the aqueous solution.

The peroxide affects decolorization of the sulfonic acid by reacting with impurities (color bodies) which may be present in trace amounts in the sulfonic acid (colored impurities present in amounts as little as 10 ppm by weight can produce intense color in sulfonic acid). The peroxide reacts with the colored bodies, converting them by oxidation to non-colored compounds. The peroxide does not react with the sulfonic acid itself. The mechanism by which this "bleaching" action is accomplished and the specific products resulting from this action are not yet fully understood. It is speculated that the exact mechanism of this reaction and the products resulting therefrom are different for each impurity present.

In the method according to the present invention, the sulfonic acids which are to be decolorized may be treated as neat liquids or, particularly when the sulfonic acid is a solid at normal temperatures, may be dissolved in an inert diluent (i.e., non-reactive with the acid or the peroxide) prior to being subjected to the decolorization treatment. Suitable inert diluents which may be employed for this purpose include low boiling point straight chain hydrocarbons (such as n-pentane, n-hexane, n-octane, etc.) and aromatic hydrocarbons (such as benzene, toluene, xylene, etc.). In the present method, it is preferred tat the sulfonic acids which are liquids at normal temperatures be treated as neat liquids, and that the sulfonic acids which are solids at normal temperatures be treated as solutions after being dissolved in an inert diluent. The amount of inert diluent used should be the minimum amount necessary to completely dissolve the sulfonic acid to be decolorized. The inert diluent should be distilled from the sulfonic acid after completion of the decolorization treatment and recovered for reuse.

The dialkanesulfonyl or diarenesulfonyl peroxide represented by Formula II may be added to the sulfonic acid to be treated either as a pure compound or as a solution in the sulfonic acid. This, of course, depends on whether the sulfonic acid to be treated is a liquid at normal temperatures or is in an inert diluent. Such a determination can be readily made by one skilled in the art.

In accordance with the present method, the treatment of the alkanesulfonic or arenesulfonic acid with a dialkanesulfonyl or diarensulfonyl peroxide to effect decolorization, can be carried out at a temperature of from about 10° C. to about 100° C. The temperature at which the mixture is allowed to stand affects the time required to achieve the desired decolorization. Generally, the time required for the desired decolorization decreases as the temperature at which the mixture is allowed to stand increases. However, side reactions which consume the dialkanesulfonyl or diarenesulfonyl peroxide also increase as the temperature is increased. Therefore, it is preferred that the mixture be allowed to stand at a temperature of from about 25° C. to about 60° C., and it is more preferred that the mixture be allowed to stand at a temperature of from about 25° C. to about 35° C., from the point of view of decreasing both the amount of time required for the desired decolorization and the number of side reactions.

In the present method, stirring or agitation is not required. However, stirring or agitation will facilitate dissolution of the peroxide in the sulfonic acid, thereby facilitating the decolorization of the sulfonic acid. Once the peroxide is dissolved in the sulfonic acid, no further agitation is required.

Also, in the method according to the present invention, the concentration of the dialkanesulfonyl or diarenesulfonyl peroxide used to effect decolorization of the alkanesulfonic or arenesulfonic acid may vary. The concentration of the dialkanesulf only or diarenesulfonyl peroxide depends in part upon the amount of colored matter present in the sulfonic acid. However, in general, the concentration of the dialkanesulfonyl or diarenesulfonyl peroxide to be mixed with the alkanesulfonic or arenesulfonic acid is from about 0.01 to about 0.5% by weight, and preferably from about 0.02% to about 0.2% by weight, of the sulfonic acid to be decolorized.

The amount of time which will be required to effect decolorization of the alkanesulfonic or arenesulfonic acid represented by Formula I according to the method of this invention is again variable, and will depend upon the amount of colored matter present in the sulfonic acid, the temperature at which the decolorizing treatment is performed (i.e., the temperature at which the mixture of the alkanesulfonic or arenesulfonic acid and dialkanesulfonyl or diarenesulfonyl peroxide is allowed to stand), the concentration of the dialkanesulfonyl or diarenesulfonyl peroxide which is employed, the desired degree of decolorization of the sulfonic acid, etc. Therefore, the time required for decolorization of the sulfonic acid to the desired level can be highly variable. For example, the color of methane sulfonic acid is acceptable at a level of APHA 150 (approximately 2 on the Gardner scale) which has been consistently achieved within less than about 70 hours using the present invention with highly colored methanesulfonic acid. However, decolorization of such sulfonic acids to essentially water white (APHA less than about 50) has consistently required times over 100 hours. Accordingly, it is difficult to specify with any certainty the time requirements according to the present invention.

However, in general, the time required to effect substantial decolorization of the sulfonic acid will be between about 1 hour and about 1 week, if the decolorization is carried out at a temperature of 25° C. For highly colored sulfonic acids, water whiteness can generally be achieved within less than two weeks or approximately 300 hours.

Performing the decolorization treatment at higher temperatures (i.e., higher than 25° C.) will generally decrease the amount of time required to effect the desired decolorization. In performing the process of the present invention, the amount of time required to effect the desired degree of decolorization of the alkanesulfonic or arenesulfonic acid will be readily determined by those skilled in the art.

However, in view of the occasionally long time periods required for the decolorization treatment to be effective, in practice it is preferred that the dialkanesulfonyl or diarenesulfonyl peroxide be added to the alkanesulfonic or arenesulfonic acid and/or the mixture be allowed to stand in the container in which the sulfonic acid will either be stored or shipped, in order to effect decolorizaion during storage or shipment. This method is particularly preferred when the sulfonic acid to be decolorized is a liquid at normal temperatures and is being treated as a neat liquid.

Although the method of the present invention may require somewhat prolonged periods of time to effect the decolorization of alkanesulfonic or arenesulfonic acids, it has an important advantage over the prior art methods which have heretofore been employed for decolorizing sulfonic acids, in that it does not introduce undesirable impurities, particularly water and sulfuric acid, into the purified sulfonic acid and does not result in the formation of impurities during the decolorization process.

In general, for methanesulfonic acid, the color of the acid may be higher than 500 on the APHA scale and 10 on the Gardner scale prior to treatment. After treatment with the present method, the color of the acid may be reduced to about 10-50 on the APHA scale and less than 1 on the Gardner scale (essentially water white). However, there is no generally accepted satisfactory final color level. The final color level which will be found to be satisfactory will depend on the sulfonic acid which is to be decolorized and the application for which the product sulfonic acid will be used.

The method of the present invention will now be illustrated by reference to the following specific, non-limiting examples.

EXAMPLE 1

Dimethanesulfonyl peroxide (0.08 grams) was added to 50 ml 773.2 grams) of dark, highly colored crude substantially anhydrous methanesulfonic acid (color >>500 on the APHA scale and about 10 on the Gardner scale) in a glass serum vial. The mixture was allowed to stand at 20° to 25° C. with occasional agitation. The color of the acid was periodically measured using a color comparator. The color was reduced to about APHA 140 (about 1–2 on the Gardner scale) within 75 hours and further to about APHA 50 (<1 on the Gardner scale, and essentially water white) within about two weeks.

EXAMPLE 2

Dimethanesulfonyl peroxide (0.146 gram) was added to 50 ml (73.43 grams) of dark, highly colored crude substantially anhydrous methanesulfonic acid (color >>500 on the APHA scale and about 10 on the Gardner scale) in a glass serum vial. The mixture was swirled occasionally to dissolve the dimethanesulfonyl peroxide and then was allowed to stand at a temperature of from about 22° to 25° C. The color of the methanesulfonic acid was periodically measured as in Example 1. The color of the acid was reduced to about 10 on the APHA scale (less than 1 on the Gardner scale, and essentially water white) within about 90 hours.

The present invention may be embodied in other specific forms without departing from the spirit or essential attributes thereof and, accordingly, reference should be made to the appended claims, rather than to the foregoing specification as indicating the scope of the invention.

What is claimed:

1. A method for decolorizing a color-contaminated alkanesulfonic or arenesulfonic acid represented by Formula I:

$$RSO_3H \qquad \qquad I$$

which comprises mixing said color-contaminated alkanesulfonic or arenesulfonic acid with an effective amount of a dialkanesulfonyl or diarenesulfonyl peroxide represented by Formula II:

$$R^1SO_2-O-O-O_2SR^1 \qquad \qquad II$$

and allowing the mixture to stand at a temperature and for a period of time sufficient to allow the color of said alkanesulfonic or arenesulfonic acid to decrease to the desired level, wherein R in Formula I and $R^1$ in Formula II are alkyl radicals or aryl radicals, with the proviso that R in Formula I may be the same as or different from $R^1$ in Formula II.

2. The method according to claim 1, wherein said color-contaminated alkanesulfonic or arenesulfonic acid is substantially anhydrous.

3. The method according to claim 1, wherein the alkyl radical or aryl radical represented by R in Formula I is the same as that represented by $R^1$ in Formula II.

4. The method according to claim 3, wherein said acid is selected from the group consisting of methanesulfonic acid, ethanesulfonic acid, propanesulfonic acid, butanesulfonic acid, octanesulfonic acid, and dodecanesulfonic acid, and said peroxide is the corresponding dialkylsulfonyl peroxide.

5. The method according to claim 3, wherein said acid is selected from the group consisting of benzenesulfonic acid, toluenesulfonic acid, dodecylbenzenesulfonic acid, and naphthalenesulfonic acid, and said peroxide is the corresponding diarenesulfonyl peroxide.

6. The method according to claim 1, wherein R and $R^1$ are alkyl radicals having from 1 to about 12 carbon atoms, or aryl radicals having from 6 to about 18 carbon atoms.

7. The method according to claim 1, wherein said mixture is allowed to stand at a temperature of from about 10° C. to about 100° C.

8. The method according to claim 1, wherein said mixture is allowed to stand at a temperature of from about 25° C. to about 60° C.

9. The method according to claim 1, wherein said mixture is allowed to stand at a temperature of from about 25° C. to about 35° C.

10. The method according to claim 1, wherein said peroxide is added to said acid in a concentration of from about 0.01 to about 0.5% by weight of the acid.

11. The method according to claim 1, wherein said peroxide is added to said acid in a concentration of from about 0.02 to about 0.2% by weight of the acid.

12. The method according to claim 1, wherein said mixture is allowed to stand for about 1 hour of about 1 week.

13. The method according to claim 1, wherein said acid and said peroxide are allowed to stand in the container in which said sulfonic acid will be stored or shipped.

14. The method according to claim 1, wherein the color of said acid is reduced to about 10 to 50 on the APHA scale.

15. The method according to claim 1, wherein said acid is a liquid and is mixed with said peroxide as a neat liquid.

16. The method according to claim 1, wherein said acid is a solid and is dissolved in an inert diluent prior to mixing with said peroxide.

17. The method according to claim 16, wherein said inert diluent is a low boiling point straight-chain hydrocarbon.

18. The method according to claim 17, wherein said low boiling point straight-chain hydrocarbon is selected from the group consisting of n-pentane, n-hexane, and n-octane.

19. The method according to claim 16, wherein said inert diluent is an aromatic hydrocarbon.

20. The method according to claim 19, wherein said aromatic hydrocarbon is selected from the group consisting of benzene, toluene, and xylene.

21. A method for decolorizing a color-contaminated methanesulfonic acid, which comprises mixing said color-cotaminated methanesulfonic acid with 0.02 to 0.2% by weight of dimethanesulfonyl peroxide, and allowing the mixture to stand at a temperature of from about 25° C. to 35° C. for a period of time sufficient to allow the color of said methanesulfonic acid to decrease to the desired level.

* * * * *